(12) United States Patent
Schultheiss et al.

(10) Patent No.: US 10,717,045 B2
(45) Date of Patent: Jul. 21, 2020

(54) REMOVAL OF OXYGEN FROM HYDROCARBON-CONTAINING GAS MIXTURES

(71) Applicant: Wacker Chemie AG, München (DE)

(72) Inventors: Peter Schultheiss, Burghausen (DE); Willibald Dafinger, Röhrnbach (DE); Marc Eckert, Julbach (DE); Friedrich Frank, Julbach (DE)

(73) Assignee: Wacker Chemie AG, Munich (DE)

( * ) Notice: Subject to any disclaimer, the term of this patent is extended or adjusted under 35 U.S.C. 154(b) by 284 days.

(21) Appl. No.: 15/527,572

(22) PCT Filed: Nov. 12, 2015

(86) PCT No.: PCT/EP2015/076374
§ 371 (c)(1),
(2) Date: May 17, 2017

(87) PCT Pub. No.: WO2016/078993
PCT Pub. Date: May 26, 2016

(65) Prior Publication Data
US 2017/0341023 A1    Nov. 30, 2017

(30) Foreign Application Priority Data
Nov. 20, 2014   (DE) .................. 10 2014 223 759

(51) Int. Cl.
| | | |
|---|---|---|
| *B01D 53/86* | (2006.01) | |
| *C07C 7/148* | (2006.01) | |
| *B01J 23/52* | (2006.01) | |
| *B01D 53/94* | (2006.01) | |

(52) U.S. Cl.
CPC ....... *B01D 53/8671* (2013.01); *B01D 53/944* (2013.01); *B01J 23/52* (2013.01); *C07C 7/14841* (2013.01); *C07C 7/14883* (2013.01); *B01D 2255/106* (2013.01); *B01D 2255/1021* (2013.01); *B01D 2255/1023* (2013.01); *B01D 2255/1025* (2013.01); *B01D 2255/1026* (2013.01); *B01D 2256/24* (2013.01); *B01D 2257/104* (2013.01); *Y02P 20/51* (2015.11); *Y02P 20/52* (2015.11)

(58) Field of Classification Search
None
See application file for complete search history.

(56) References Cited

U.S. PATENT DOCUMENTS

| | | | |
|---|---|---|---|
| 3,124,416 A * | 3/1964 | Cohn et al. ............ | B01D 53/46 |
| | | | 423/219 |
| 4,093,559 A | 6/1978 | Fernholz et al. | |
| 4,093,703 A | 6/1978 | Buechner et al. | |
| 5,442,329 A | 6/1995 | Wirtz et al. | |
| 5,466,232 A | 11/1995 | Cadieux et al. | |
| 2007/0004926 A1 | 1/2007 | Schindler et al. | |
| 2008/0183024 A1 | 7/2008 | Klanner et al. | |
| 2010/0022796 A1 | 1/2010 | Heidenreich et al. | |
| 2010/0048972 A1 | 2/2010 | Sun et al. | |
| 2011/0113774 A1* | 5/2011 | Nunn ...................... | F01N 3/08 |
| | | | 60/605.1 |
| 2012/0003132 A1* | 1/2012 | Wang ..................... | B01J 23/002 |
| | | | 423/219 |
| 2014/0316181 A1* | 10/2014 | Averlant ................. | C07C 7/163 |
| | | | 585/850 |

FOREIGN PATENT DOCUMENTS

| | | |
|---|---|---|
| DE | 102006058800 A1 | 6/2008 |
| EP | 0499087 A1 | 8/1992 |
| EP | 0565952 A1 | 10/1993 |
| EP | 2656904 A1 | 10/2013 |
| GB | 565991 | 12/1944 |
| GB | 883945 | 12/1961 |
| JP | 2000281327  * | 10/2000 |
| WO | 2006075025 A1 | 7/2006 |
| WO | 2014006017 A1 | 1/2014 |

OTHER PUBLICATIONS

International Search Report and Written Opinion for International Application No. PCT/EP2015/076374, dated Jan. 21, 2016, 8 pages.
Hosseini et al., "Promotional effect of gold added to palladium supported on a new mesoporous TiO2 for total oxidation of volatile organic compounds", Catalysis Today, 2007, vol. 122, pp. 391-396.
van de Beld et al., "A kinetic study of the complete oxidation of ethene, propane and their mixtures on a Pd/Al2O3 catalyst", Chemical Engineering and Processing, 1995, vol. 34, pp. 469-478.
Rusu et al., "Destruction of Volatile Organic Compounds by Catalytic Oxidation", Environmental Engineering and Management Journal, Dec. 2003, vol. 2, No. 4, pp. 273-302.

* cited by examiner

Primary Examiner — Sheng H Davis
(74) Attorney, Agent, or Firm — RatnerPrestia

(57) ABSTRACT

The invention relates to a method for removing oxygen from hydrocarbon-containing gas mixtures, characterized in that a hydrocarbon-containing gas mixture containing 50 vol % of one or more hydrocarbons, 2 to 10 vol % of oxygen, and possibly one or more gases from the group comprising nitrogen, noble gases, hydrogen, carbon dioxide, carbon monoxide, and water is introduced into an isothermally operated reactor, in which the oxygen contained in the hydrocarbon-containing gas mixture is at least partially converted into carbon dioxide and water in the presence of one or more catalysts, wherein the specifications in vol % relate to the total volume of the hydrocarbon-containing gas mixture introduced into the reactor and add up to 100 vol % in total.

10 Claims, 1 Drawing Sheet

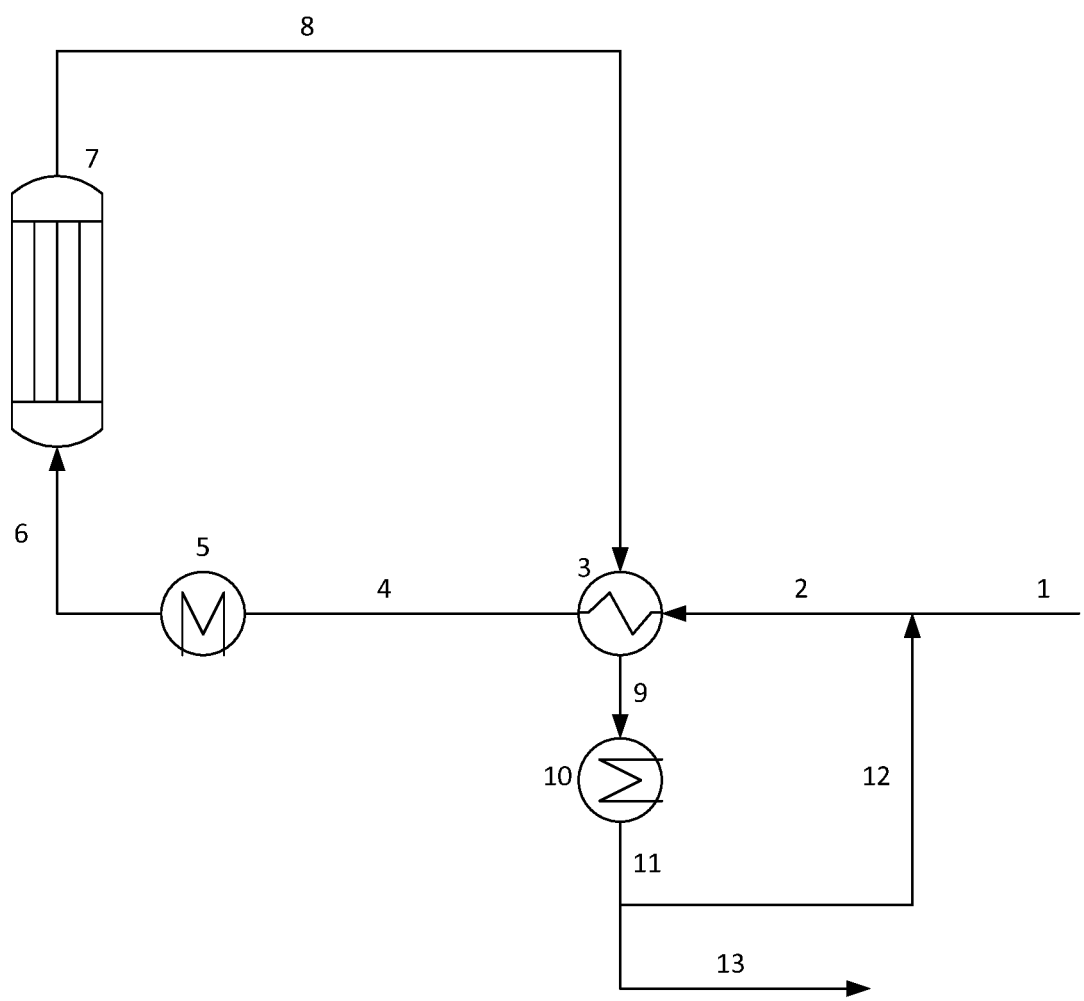

REMOVAL OF OXYGEN FROM HYDROCARBON-CONTAINING GAS MIXTURES

CROSS-REFERENCE TO RELATED APPLICATIONS

This application is a U.S. National Phase Application of PCT International Application PCT/EP2015/076374, filed Nov. 12, 2015, which claims priority benefit of German Application DE 10 2014 223 759.9, filed Nov. 20, 2014, the disclosures of which are incorporated herein in their entirety.

BACKGROUND

The invention relates to a process for removing oxygen from hydrocarbon-containing gas mixtures.

Hydrocarbons such as ethylene, propylene or other hydrocarbons having from 1 to 7 carbon atoms are standard basic chemicals of the chemical industry. Gases of such hydrocarbons often contain impurities, for example oxygen, which can be a hindrance in the utilization of the hydrocarbon gases and in such cases should be at least partly removed from the hydrocarbon gases. A customary purification method is cryodistillation. However, this method is problematical for oxygen-containing hydrocarbon gases since such mixtures cannot be sufficiently separated by distillation and an accumulation of oxygen can instead occur when impurities are distilled off. In addition, cocondensation of hydrocarbon gases and oxygen can occur in cryodistillation, which is very problematical from a safety point of view. Accumulation of oxygen in hydrocarbon gases has to be avoided at all costs since oxygen is a hindrance for many uses of hydrocarbon gases and, particularly problematically, unstable or even explosive gas mixtures can be formed. In the membrane process too, sufficient separation does not occur, which can lead to accumulation of oxygen in the retentate or permeate and thus again to formation of explosive oxygen-containing gas mixtures.

The oxidative purification of gas mixtures, in which hydrocarbons and oxygen of the gas mixture are reacted with one another to form products which are not a hindrance or can easily be separated off, e.g. carbon dioxide and water, is also known. However, these reactions are strongly exothermic. The oxidative purification has found widespread use for gas mixtures which contain very small amounts of hydrocarbons and/or very small amounts of oxygen, for example industrial offgases or exhaust gases from automobiles. In the case of gas mixtures which contain relatively large proportions both of hydrocarbons and also of oxygen, heat is liberated in the oxidative purification in such considerable amounts that the formation of undesirable by-products or decomposition products or even an explosive oxidation reaction is to be expected.

In order to be able to carry out the oxidative purification at relatively low reaction temperatures, use has frequently been made of catalysts, for example ruthenium catalysts. However, even catalysts require certain minimum temperatures, the "light off" temperature, in order to obtain their catalytic activity, and these continue to be in a range which is problematical from a safety point of view in the case of gas mixtures having high contents of hydrocarbons and oxygen.

Thus, for example, U.S. Pat. No. 4,093,703 describes the oxidative removal of ethylene from gas mixtures containing up to 1.8% by volume of ethylene. US 2010/0048972 teaches the use of ruthenium catalysts for purifying ethylene from crackers. The oxygen content of the gases to be purified described therein is in the ppm range. US 2010/0048972 advises against the use of palladium catalysts for oxygen removal. EP 0499087 is concerned with the removal of traces of nitrogen oxide, carbon monoxide and hydrocarbons from oxygen-rich exhaust gases from gas turbines. The exhaust gases consist essentially of nitrogen. GB 883945 describes methods of purifying offgases from the oxidative reaction of ammonia to form nitric acid, in which nitrogen oxides and oxygen are removed by addition of unsaturated compounds and sulfides. These offgases, too, consist essentially of nitrogen. In Chemical Engineering and Processing 34, (1995), pages 469 to 478, van de Beld describes the total oxidation of ethene and propane over Pd catalysts supported on $Al_2O_3$. Rusu also discusses the oxidation of ethene in Environmental Engineering and Management Journal, 2003, Vol. 2, No. 4, pages 273 to 302. The most frequently used catalyst systems here are Pd or Pt on $TiO_2$, $Al_2O_3$ or $SiO_2$. In Catalysis Today, 122, (2007), pages 391 to 396, Hosseini recommends Pd and Au on $TiO_2$ as catalyst for the total oxidation of propene. Catalysts for purifying exhaust gases from diesel engines are known from EP 2656904. The catalysts contain a catalytic coating comprising Pt, Pd and a carbon-storing compound such as zeolite and also a further coating comprising Pd and Au.

Owing to the fact that the handling and purification of hydro-carbon gases which are contaminated with considerable amounts of oxygen continue to present problems, such gas mixtures are frequently incinerated, which is fatal from an economic point of view since hydrocarbons such as ethylene are valuable petrochemical starting materials.

SUMMARY

In light of this background, it was an object of the invention to provide processes for the oxidative removal of oxygen from gas mixtures which consist mostly of hydrocarbons and contain considerable proportions of oxygen. Here, the abovementioned problems should be able to be solved and in particular the formation of by-products should be able to be minimized and explosions should be able to be prevented. If possible, hydrocarbon gases comprising gas mixtures which are variable over time, in particular variable proportions of oxygen and/or hydrocarbons, should also be able to be purified oxidatively in a continuous reaction process.

The invention provides processes for removing oxygen from hydrocarbon-containing gas mixtures, characterized in that a hydrocarbon-containing gas mixture containing ≥50% by volume of one or more hydrocarbons, from 2 to 10% by volume of oxygen and optionally one or more gases from the group consisting of nitrogen, noble gases, hydrogen, carbon dioxide, carbon monoxide and water is introduced into an isothermally operated reactor in which the oxygen present in the hydrocarbon-containing gas mixture is at least partly converted into carbon dioxide and water in the presence of one of more catalysts, where the figures in % by volume are based on the total volume of the hydrocarbon-containing gas mixture introduced into the reactor and add up to a total of 100% by volume.

The combined use of catalysts and isothermally operated reactors surprisingly allows the controlled oxidative purification of oxygen- and hydrocarbon-rich gas mixtures.

The hydrocarbon-containing gas mixtures will hereinafter also be referred to as gas mixtures for short.

BRIEF DESCRIPTION OF THE DRAWINGS

FIG. 1 is a schematic flow diagram of the plant used to carry out the oxidative purification process described in Example 1.

DETAILED DESCRIPTION

In the process of the invention, hydrocarbons of the gas mixture to be purified are generally reacted oxidatively by the oxygen present as impurity in the gas mixture, so that the oxygen content in the gas mixture is reduced. Thus, a reaction of oxygen with hydrocarbons to form carbon dioxide and water generally takes place in the reactor. The process can thus be referred to as oxidative self purification.

The hydrocarbons preferably have from 1 to 7 carbon atoms, particularly preferably from 1 to 5 carbon atoms and most preferably from 1 to 3 carbon atoms. The hydrocarbons are preferably present in the form of a gas at a pressure of 1 $bar_{abs.}$. The hydrocarbons have boiling points at a pressure of 1 $bar_{abs.}$ of preferably ≤−20° C., particularly preferably ≤−40° C. and most preferably ≤−60° C. The hydrocarbons can be saturated or preferably ethylenically unsaturated. Examples of saturated hydrocarbons are methane, ethane, propane, butane or pentane. Examples of ethylenically unsaturated hydrocarbons are propene, butadiene, acetylene and in particular ethylene.

The hydrocarbons preferably do not bear any functional groups such as alcohol groups or halides, in particular do not bear any functional groups containing oxygen atoms, sulfur atoms, halogen atoms or nitrogen atoms. The hydrocarbons preferably consist exclusively of carbon atoms and hydrogen atoms or isotopes thereof. Particularly preferred hydrocarbons are ethylenically unsaturated hydrocarbons, in particular ethylene.

Examples of noble gases are helium, neon, krypton, xenon, radon and in particular argon.

The hydrocarbon-containing gas mixture which is to be purified and is introduced into the isothermal reactor contains ≥50% by volume, preferably from 60 to 93.5% by volume, particularly preferably from 65 to 90% by volume, even more preferably from 65 to 85% by volume and most preferably from 70 to 80% by volume, of one or more hydrocarbons. Saturated hydrocarbons, in particular methane or ethane, are here preferably present in an amount of from 0.1 to 10% by volume and particularly preferably from 3 to 6% by volume. The gas mixture contains oxygen in proportions of ≤10% by volume, preferably ≤6.5% by volume, particularly preferably ≤5% by volume and most preferably ≤4% by volume. Oxygen is present in proportions of ≥2% by volume, preferably ≥3% by volume and particularly preferably ≥4% by volume, in the gas mixture. The remaining proportions of the gas are the further gases selected from the group consisting of nitrogen, noble gases, hydrogen, carbon dioxide, carbon monoxide and water. The figures in % by volume are based on the total volume of the respective gas mixture and add up to a total of 100% by volume.

The hydrocarbon-containing gas mixtures preferably do not contain any hydrogen.

As reactor, use is generally made of a tube reactor or shell-and-tube reactor. The gas mixture is preferably reacted in tubes around which a coolant flows. Possible coolants, are, for example, oil or salt solutions or water. Preference is given to evaporative water cooling. The temperature in the reactor can be regulated in this way. Such reactors and their design are well known to a person skilled in the art. a The reactor is operated isothermally or preferably not adiabatically. However, this does not rule out hot spots being able to arise within the reactor, in particular in isolated places or locally or occasionally. Hot spots are local overheating occurrences or temperature maxima which, however, level off during operation of the reactor. The temperature of the gas mixture exiting from the reactor differs from the temperature of the gas mixture entering the reactor by preferably ≤50° C., more preferably ≤30° C., particularly preferably ≤25° C., even more preferably ≤20° C. and most preferably ≤15° C.

The reactor is generally provided with one or more catalysts, for example, as fixed-bed catalyst. The catalysts generally contain noble metals or salts thereof. Examples of noble metals are rhodium, ruthenium, with preference being given to gold, palladium and/or platinum, in particular palladium/gold or platinum/gold. The noble metals (salts) can have been applied to supports (supported catalysts). Examples of supports are oxides of metals or semimetals, e.g. zirconium, titanium, cerium, lanthanum or in particular aluminum or silicon. Particular preference is given to silica, aluminum oxides or bentonite.

Furthermore, the catalysts can contain one or more dopants, for example inorganic salts such as halides, oxides, nitrates, nitrites, silicates, carbonates, borates, aluminates, molybdates, tungstates, vanadates, niobates, tantalates, titanates or zirconates.

The catalysts can be produced by methods known per se as are described, for example, in DE 102006058800 A1, U.S. Pat. No. 4,093,559 or EP 565952.

The reactor is supplied with the gas mixture. The reactor is preferably operated continuously. The gas mixture can be passed a plurality of times through the reactor. However, it is generally sufficient to pass the gas mixture once through the reactor.

The reactor can be configured so that the flow direction of the gas mixture in the reactor is substantially horizontal or preferably substantially vertical. In the case of a vertical flow direction, the gas mixture can flow through the reactor from the top downward or preferably from the bottom upward. The preferred variants are particularly useful for achieving the object of the invention and for the efficient removal of the heat from the reactor.

Preference is given to no agent which serves or could serve for purification, in particular no additional oxygen and/or no reducing agent such as hydrogen or hydrocarbons, being added to the gas mixtures to be purified. Thus, preference is given to nothing which is different from the hydrocarbon-containing gas mixtures to be purified by the process of the invention being added to the gas mixtures.

Preferences is given to no further gas and/or no further agent, in particular no oxygen or hydrogen, being introduced into the reactor. Thus, preference is given to exclusively the gas mixture to be purified being introduced into the reactor while carrying out the process of the invention.

The gas mixture has a temperature of preferably ≤300° C., more preferably ≤250° C., particularly preferably ≤230° C., more particularly preferably ≤210° C. and most preferably ≤200° C., on entry or immediately before entry into the reactor. The temperature here is preferably ≥100° C., particularly preferably ≥120° C., even more preferably ≥150° C. and most preferably ≥180° C.

The gas mixture which is introduced into the reactor can be brought to the desired temperature by means of one or more heat exchangers. Examples of heat exchangers are plate heat exchangers, (shell-and-)tube heat exchangers, U-tube heat exchangers, jacket tube heat exchangers, heating registers or countercurrent film heat exchangers. Preference is given to (shell-and-)tube heat exchangers. The medium of the heat exchanger is preferably oil or salt solutions or water.

The gas mixture leaving the reactor has a temperature of preferably ≤350° C., particularly preferably ≤300° C., even more preferably ≤250° C. and most preferably ≤230. The temperature here is preferably ≥100° C., particularly preferably ≥150° C. and most preferably ≥180° C. The exiting gas mixture is generally hotter than the gas mixture introduced into the reactor.

The gas mixture leaving the reactor contains oxygen in proportions of preferably ≤1.5% by volume, more preferably ≤1% by volume, particularly preferably ≤0.5% by volume, even more preferably ≤0.1% by volume and most preferably ≤0.00001% by volume. The proportion of hydrocarbons is preferably from 55 to 95% by volume, particularly preferably from 60 to 90% by volume und and most preferably from 65 to 80% by volume. In an alternative embodiment, the proportion of hydrocarbons is preferably from 60 to 99.99999% by volume, particularly preferably from 80 to 99.99% by volume, even more preferably from 90 to 99.99% by volume and most preferably from 95 to 99.9% by volume. The remaining parts of the gas are made up of the further gases selected from the group consisting of nitrogen, noble gases, hydrogen, carbon dioxide, carbon monoxide and water. The figures in % by volume are in each case based on the total volume of the respective gas mixture and add up to a total of 100% by volume.

The degree of conversion of oxygen is preferably from 50 to 100 mol %, particularly preferably from 80 to 100 mol %, even more preferably from 90 to 100 mol % and most preferably from 95 to 100 mol %. The degree of conversion is for the present purposes the molar ratio of the number of moles of oxygen which were reacted in the reactor and the number of moles of oxygen which were present in the gas mixture before or on entry into the reactor. The degree of conversion here preferably relates to the reaction of oxygen with hydrocarbons to form carbon dioxide and water.

After leaving the reactor, the gas mixture preferably contains from 85 to 99% by weight, particularly preferably from 92 to 98% by weight and most preferably from 95 to 97% by weight, of the hydrocarbons present in the gas mixture to be purified before entry into the reactor.

The gas mixture which has left the reactor can be passed directly to its utilization. Ethylene-containing gas mixtures can, for example, be used for preparing vinyl chloride, acetaldehyde, ethylene oxide or in particular vinyl acetate.

As an alternative, the gas mixture which has left the reactor can be purified further, for example by means of distillation such as cryodistillation, membrane purification processes or adsorption processes such as scrubbing processes. Carbon dioxide is preferably separated off by means of alkaline water scrubbers.

The method of carrying out such processes for utilization or purification of hydrocarbon gases is known to those skilled in the art.

In a preferred embodiment, the gas mixture which has left the reactor is passed through a countercurrent heat exchanger. A gas mixture which is fed to the reactor is preferably heated in the countercurrent heat exchanger. In this way, the energy efficiency of the process can be increased.

The gas mixture which leaves the countercurrent heat exchanger and is fed to the reactor is preferably heated by from 20 to 200° C., particularly preferably from 70 to 180° C. and most preferably from 100 to 170° C., in the countercurrent heat exchanger.

In a further preferred embodiment, part of the gas mixture which has left the reactor is added to a starting gas mixture and the remaining part is passed to the further purification or utilization. The abovementioned part which is added to a starting gas mixture will hereinafter also be referred to as recycle gas. The recycle gas is here preferably taken from a gas mixture which has flowed through one or more heat exchangers, in particular one or more countercurrent heat exchangers. The gas mixture has particularly preferably flowed through one or more countercurrent heat exchangers and at a later point in time through one or more further heat exchangers.

The gas mixture obtained in this way from the starting gas mixture and the recycle gas can, in order to remove oxygen, be introduced into an isothermally operated reactor in which the oxygen present in the gas mixture is at least partly converted into carbon dioxide and water in the presence of one or more catalysts, as described above.

The proportion of the recycle gas is preferably from 0% by volume to 95% by volume, particularly preferably from 40% by volume to 85% by volume and most preferably from 60% by volume to 80% by volume, based on the total volume of the gas mixture leaving the reactor.

The embodiment encompassing the recycle gas has the advantage that it is possible to purify starting gas mixtures which have such high oxygen contents that they would, for example, be explosive under the conditions in the reactor, without further extraneous gas streams or further safety measures being necessary or undesirable by-products being formed in the procedure according to the invention. This considerably increases the flexibility of the process for use for a wide variety of gas mixtures or for gas mixtures having a composition which varies over time. Even during start-up or running down of plants, it can be ensured in this way that the oxidative purification occurs safely.

The starting gas mixtures preferably contain ≤15% by volume, particularly preferably ≤12% by volume and most preferably ≤11% by volume, of oxygen. Preference is given to ≥4% by volume, more preferably ≥5% by volume, particularly preferably ≥6.5% by volume and most preferably 7% by volume, of oxygen. The oxygen content of the starting gas mixture is, in the respective process, generally greater than the oxygen content of the gas mixture introduced into the reactor. The starting gas mixture preferably contains from 40 to 95% by volume, particularly preferably from 50 to 90% by volume, even more preferably from 60 to 85% by volume and most preferably from 65 to 80% by volume, of one or more hydrocarbons. Saturated hydrocarbons, in particular methane or ethane, are preferably present in amounts of from 0.1 to 10% by volume and particularly preferably from 3 to 6% by volume. The remaining parts of the gas are made up of the further gases selected from the group consisting of nitrogen, noble gases, hydrogen, carbon dioxide, carbon monoxide and water. The figures in % by volume are based on the total volume of the respective gas mixture and add up to a total of 100% by volume.

Such starting gas mixtures, in particular ethylene-containing gas mixtures, can be obtained, for example, in the preparation of vinyl chloride, ethylene oxide or in particular in the catalytic preparation of vinyl acetate from ethylene, acetic acid and oxygen.

The starting gas mixtures have temperatures of preferably from 0 to 100° C., particularly preferably from 10 to 80° C. and most preferably from 20 to 60° C.

The gas mixture obtained after mixing of the recycle gas and the starting gas mixture preferably contains ≥50% by volume, more preferably from 60 to 93.5% by volume, particularly preferably from 65 to 90% by volume, even more preferably from 65 to 85% by volume and most preferably from 70 to 80% by volume, of one or more hydrocarbons.

Saturated hydrocarbons, in particular methane or ethane, are here preferably present in amounts of from 0.1 to 10% by volume and particularly preferably from 3 to 6% by volume. The gas mixture contains oxygen in proportions of preferably ≤10% by volume, more preferably ≤6.5% by volume, particularly preferably ≤5% by volume and most preferably ≥4% by volume. Oxygen is present in proportions of preferably ≥2% by volume, particularly preferably ≥3% by volume and most preferably ≥4% by volume, in the gas mixture. The remaining parts of the gas are made up of the further gases selected from the group consisting of nitrogen, noble gases, hydrogen, carbon dioxide, carbon monoxide and water. The figures in % by volume are based on the total volume of the respective gas mixture and add up to a total of 100% by volume.

One or more heat exchangers can optionally be installed at various places in the process of the invention, preferably upstream of the reactor and/or downstream of the reactor. Particular preference is given to a heat exchanger being physically located between the countercurrent heat exchanger and the reactor. Particular preference is also given to a heat exchanger being physically located downstream of the counter-current heat exchanger and upstream of the point at which the recycle gas is separated off.

All gas mixtures have a pressure of preferably from 3 to 20 $bar_{abs.}$, particularly preferably from 5 to 15 $bar_{abs.}$ and most preferably from 8 to 12 $bar_{abs.}$, in the process of the invention. The abovementioned pressures prevail particularly in the reactor and/or in any heat exchangers and/or in the conduits through which the gas mixtures are conveyed. The process is preferably carried out at substantially constant pressures. The pressure fluctuations of the gas mixtures are preferably ≤5 $bar_{abs.}$, particularly preferably ≤2 $bar_{abs.}$, and most preferably ≤1 $bar_{abs.}$. Pressure fluctuations here refer to the pressure difference between pressure maxima and pressure minima. Compressors can optionally be installed at one or more places in the process of the invention, in particular in the case of the recycle gas variant.

In the respective specific embodiment of the process of the invention, the gas composition, pressure and temperature are generally selected so that the gas mixture remains below the ignition limit, preferably in accordance with DIN EN 1839-13. The use of the measures of DIN EN 1839-13 is well known to those skilled in the art.

The process of the invention makes it possible to free hydro-carbon-containing gas mixtures completely or at least partly of oxygen. The hydrocarbon gases after the purification according to the invention has been carried out generally consists essentially of hydrocarbons and generally contain not more than traces of oxygen.

The process of the invention advantageously allows hydrocarbon gas mixtures which have high oxygen contents and are highly problematical from a safety point of view to be converted into easily handable and economically interesting, useful gas mixtures. Conditions which are of concern from a safety point of view can here be avoided, and the desired oxidative purification of hydrocarbon-containing gas mixtures can nevertheless be carried out. The gas mixtures can be handled at every stage of the process under conditions such as gas composition, pressure and temperature which are below the ignition limit in accordance with DIN EN 1839-13 and thus in the safe range. It was also particularly surprising that the oxidative purification could be carried out in the reactor at relatively low temperatures. In addition, the formation of undesirable by-products can be suppressed or even entirely eliminated. Furthermore, the oxygen present in the hydrocarbon gas can be converted completely or nearly completely into carbon dioxide and water. For all these advantages, the mode of operation of the reactor and also the conducting and treatment of the gas streams worked synergistically with one another.

The following examples serve to further illustrate the invention:

EXAMPLE 1 (EX. 1)

The oxidative purification of the gas mixture was carried out in a plant as shown in FIG. 1. Data on the compositions, temperature and pressures of the gas mixture in the various parts of plant may be found in tables 1 and 2.

The gas mixture 1, i.e. a starting gas mixture, was mixed with the gas mixture 12, i.e. a recycle gas. The gas mixture 2 obtained in this way was passed through the countercurrent heat exchanger 3. Here, heat was transferred from the gas mixture 8 to the gas mixture 2. The gas mixture 4 which had been heated in this way was conveyed for further heating through the heat exchanger 5 operated by means of superheated steam and introduced as further-heated gas mixture 6 into the shell-and-tube reactor 7. The shell-and-tube reactor 7 was provided with a supported palladium-gold fixed-bed catalyst and was operated isothermally by means of evaporative water cooling.

The oxygen conversion in the shell-and-tube reactor 7 was 97 mol %, based on the oxygen introduced into the reactor.

The gas mixture 8 leaving the shell-and-tube reactor 7 was cooled during flow through the countercurrent heat exchanger 3 and was, to effect further cooling, conveyed through the heat exchanger 10 operated using cooling water as gas mixture 9. Water condensed out here.

77 mol % of the gas mixture 11, based on the molar flow of gas mixture 11, was mixed as recycle gas 12 with the gas mixture 1 to give gas mixture 2 and thus recirculated into the process. The remaining 23 mol % of the gas mixture 11 was passed to utilization.

The purified gas mixture 13 had a composition identical to that of the gas mixture 11 and thus contained only traces of oxygen. The formation of any by-products such as carbon monoxide or ethylene oxide was not observed. Hydrogenation of ethylene to ethane also did not occur.

TABLE 1

Compositions of the gas mixtures of example 1:

| | Ethylene [% by volume] | Oxygen [% by volume] | Carbon dioxide [% by volume] | Ethane, methane [% by volume] | Inerts[a] [% by volume] |
|---|---|---|---|---|---|
| Gas mixture 1 | 76.8 | 9.1 | 1.7 | 5.4 | 7.2 |
| Gas mixture 2 | 78.2 | 2.2 | 6.6 | 5.5 | 7.5 |
| Gas mixture 8 | 77.43 | 0.07 | 8.1 | 5.5 | 8.9 |
| Gas mixture 11 | 78.53 | 0.07 | 8.2 | 5.6 | 7.6 |

[a]Noble gases, nitrogen and water.

TABLE 2

Temperature and pressure of the gas mixtures of the examples:

|  |  | Ex. 1 | Ex. 2 | Ex. 3 | Ex. 4 | Ex. 5 |
|---|---|---|---|---|---|---|
| Gas mixture 1 | Temperature [° C.] | 25 | 50 | 30 | 25 | 25 |
|  | Pressure [$bar_{abs}$] | 10.5 | 10.5 | 9.5 | 10.5 | 10.5 |
| Gas mixture 2 | Temperature [° C.] | 28 | 40 | 30 | 29 | 29 |
|  | Pressure [$bar_{abs}$] | 10.5 | 10.5 | 9.5 | 10.5 | 10.5 |
| Gas mixture 4 | Temperature [° C.] | 175 | 175 | 175 | 190 | 190 |
|  | Pressure [$bar_{abs}$] | 10.45 | 10.45 | 9.45 | 10.45 | 10.45 |
| Gas mixture 6 | Temperature [° C.] | 195 | 195 | 195 | 220 | 220 |
|  | Pressure [$bar_{abs}$] | 10.42 | 10.42 | 9.42 | 10.42 | 10.42 |
| Gas mixture 8 | Temperature [° C.] | 215 | 205 | 215 | 230 | 230 |
|  | Pressure [$bar_{abs}$] | 10.32 | 10.32 | 9.32 | 10.32 | 10.32 |
| Gas mixture 9 | Temperature [° C.] | 78 | 78 | 78 | 80 | 80 |
|  | Pressure [$bar_{abs}$] | 10.29 | 10.29 | 9.29 | 10.29 | 10.29 |
| Gas mixture 11 | Temperature [° C.] | 25 | 25 | 25 | 25 | 25 |
|  | Pressure [$bar_{abs}$] | 10.29 | 10.29 | 9.29 | 10.29 | 10.29 |
| Gas mixture 12 | Temperature [° C.] | 25 | 25 | 25 | 25 | 25 |
|  | Pressure [$bar_{abs}$] | 10.83 | 10.83 | 9.83 | 10.83 | 10.83 |
| Gas mixture 13 | Temperature [° C.] | 25 | 25 | 25 | 25 | 25 |
|  | Pressure [$bar_{abs}$] | 10.83 | 10.83 | 9.83 | 10.83 | 10.83 |

EXAMPLE 2 (EX. 2)

Example 2 was carried out in a manner identical to example 1, with the following differences:

The gas mixture 1, i.e. the starting gas mixture, had a different composition, as indicated in table 3.

The oxygen conversion in the shell-and-tube reactor 7 was 84 mol %, based on the oxygen introduced into the reactor.

47 mol % of the gas mixture 11, based on the molar flow of gas mixture 11, was recirculated as recycle gas 12 into the process. The remaining 53 mol % of the gas mixture 11 was passed to utilization.

Further information on the compositions, temperatures and pressures of the gas mixture at the various places of the process may be found in tables 2 and 3.

TABLE 3

Compositions of the gas mixtures of example 2:

|  | Ethylene [% by volume] | Oxygen [% by volume] | Carbon dioxide [% by volume] | Ethane, methane [% by volume] | Inerts[a] [% by volume] |
|---|---|---|---|---|---|
| Gas mixture 1 | 75.0 | 11.1 | 2.0 | 5.2 | 6.7 |
| Gas mixture 2 | 75.8 | 6.5 | 5.0 | 5.4 | 7.3 |
| Gas mixture 8 | 74.0 | 1.0 | 8.7 | 5.4 | 10.9 |
| Gas mixture 11 | 76.8 | 1.0 | 9.0 | 5.6 | 7.6 |

[a]Noble gases, nitrogen and water.

EXAMPLE 3 (EX. 3)

Example 3 was carried out in a manner identical to example 1, with the following differences:

The gas mixture 1, i.e. starting gas mixture, had a different composition, as indicated in table 4.

The oxygen conversion in the shell-and-tube reactor 7 was 95 mol %, based on the oxygen introduced into the reactor.

No recycle gas 12 was taken off from the gas mixture 11; i.e. the gas mixture 11 was passed in its entirety to utilization.

Further information on the compositions, temperatures and pressures of the gas mixture at the various places of the process may be found in tables 2 and 4.

TABLE 4

Compositions of the gas mixtures of example 3:

|  | Ethylene [% by volume] | Oxygen [% by volume] | Carbon dioxide [% by volume] | Ethane, methane [% by volume] | Inerts[a] [% by volume] |
|---|---|---|---|---|---|
| Gas mixture 1 | 81.2 | 5.0 | 1.6 | 5.2 | 7.0 |
| Gas mixture 2 | 81.2 | 5.0 | 1.6 | 5.2 | 7.0 |
| Gas mixture 8 | 79.6 | 0.3 | 4.8 | 5.2 | 10.1 |
| Gas mixture 11 | 82.2 | 0.3 | 4.9 | 5.4 | 7.3 |

[a]Noble gases, nitrogen and water.

EXAMPLE 4 (EX. 4)

Example 4 was carried out in a manner identical to example 1, with the following differences:

The gas mixture 1, i.e. the starting gas mixture, had a different composition, as indicated in table 5.

The heat exchanger 5 was operated using heat transfer oil. The shell-and-tube reactor 7 was provided with a supported palladium fixed-bed catalyst instead of the palladium-gold catalyst.

The oxygen conversion in the shell-and-tube reactor 7 was 40 mol %, based on the oxygen introduced into the reactor.

92 mol % of the gas mixture 11, based on the molar flow of gas mixture 11, was recirculated as recycle gas 12 into the process. The remaining 8 mol % of the gas mixture 11 was passed to utilization.

Further information on the compositions, temperatures and pressures of the gas mixture at the various places of the process may be found in tables 2 and 4.

TABLE 5

Compositions of the gas mixtures of example 4:

|  | Ethylene [% by volume] | Oxygen [% by volume] | Carbon dioxide, Carbon monoxide [% by volume] | Ethan, methane [% by volume] | Inerts[a] [% by volume] |
|---|---|---|---|---|---|
| Gas mixture 1 | 77.7 | 8.2 | 1.7[b] | 5.4 | 7.0 |
| Gas mixture 2 | 79.1 | 1.7 | 6.3 | 5.5 | 7.4 |

TABLE 5-continued

Compositions of the gas mixtures of example 4:

| | Ethylene [% by volume] | Oxygen [% by volume] | Carbon dioxide, Carbon monoxide [% by volume] | Ethan, methane [% by volume] | Inerts[a] [% by volume] |
|---|---|---|---|---|---|
| Gas mixture 8 | 78.9 | 1.0 | 6.8 | 5.5 | 7.8 |
| Gas mixture 11 | 79.3 | 1.0 | 6.8 | 5.5 | 7.4 |

[a]Noble gases, nitrogen and water;
[b]No carbon monoxide present in the starting gas 1.

EXAMPLE 5 (EX. 5)

Example 5 was carried out in a manner identical to example 4, with the following differences:

The gas mixture 1, i.e. the starting gas mixture, had a different composition, as indicated in table 5.

The oxygen conversion in the shell-and-tube reactor 7 was 40 mol %, based on the oxygen introduced into the reactor.

91 mol % of the gas mixture 11, based on the molar flow of gas mixture 11, was recirculated as recycle gas 12 into the process. The remaining 9 mol % of the gas mixture 11 was passed to utilization.

Further information on the compositions, temperatures and pressures of the gas mixture at the various places of the process may be found in tables 2 and 4.

When a supported platinum fixed-bed catalyst was used instead of the palladium catalyst in the processes of examples 4 and 5, the results of examples 4 and 5 were essentially reproduced.

TABLE 6

Compositions of the gas mixtures of example 5:

| | Ethylene [% by volume] | Oxygen [% by volume] | Carbon dioxide, Carbon monoxide [% by volume] | Ethane, methane [% by volume] | Inerts[a] [% by volume] |
|---|---|---|---|---|---|
| Gas mixture 1 | 80.9 | 5.0 | 1.7[b] | 5.2 | 7.2 |
| Gas mixture 2 | 81.9 | 1.0 | 4.5 | 5.4 | 7.2 |
| Gas mixture 8 | 81.7 | 0.6 | 4.7 | 5.4 | 7.5 |
| Gas mixture 11 | 82.0 | 0.6 | 4.7 | 5.4 | 7.3 |

[a]Noble gases, nitrogen and water;
[b]No carbon monoxide present in the starting gas 1.

The invention claimed is:

1. A process for removing oxygen from hydrocarbon-containing gas mixtures, the hydrocarbons comprising one or more ethylenically unsaturated hydrocarbons, the process comprising the steps of:
introducing a hydrocarbon-containing gas mixture containing 60 to 93.5% by volume of one or more ethylenicallyunsaturated hydrocarbons, from 2 to 10% by volume of oxygen and optionally one or more gases from the group consisting of nitrogen, noble gases, carbon dioxide, carbon monoxide and water into an isothermally operated reactor, and at least partly converting the oxygen present in the hydrocarbon-containing gas mixture into carbon dioxide and water in the presence of one of more catalysts to produce a gas mixture exiting the reactor, wherein the gas mixture exiting the reactor contains ≤1.5% by volume of oxygen, from 55 to 99.99999% by volume of one or more hydrocarbons and optionally one or more further gases selected from the group consisting of nitrogen, noble gases, hydrogen, carbon dioxide, carbon monoxide and water,
wherein the hydrocarbon-containing gas mixture does not contain any hydrogen and no hydrogen is added to the hydrocarbon-containing gas mixture and
the one or more catalysts are selected from the group consisting of palladium/gold, platinum/gold and salts thereof,
where the percents by volume are based on the total volume of the hydrocarbon-containing gas mixture introduced into the reactor and add up to a total of 100% by volume.

2. The process for removing oxygen from hydrocarbon-containing gas mixtures as claimed in claim 1, wherein no oxygen is introduced as further gas into the reactor.

3. The process for removing oxygen from hydrocarbon-containing gas mixtures as claimed in claim 1, wherein the gas mixture exiting from the reactor has a temperature that differs from the temperature of the hydrocarbon-containing gas mixture entering the reactor by ≤50° C.

4. The process for removing oxygen from hydrocarbon-containing gas mixtures as claimed in claim 1, wherein the hydrocarbon-containing gas mixture has a temperature of from ≤300° C. to ≥100° C. on entering the reactor.

5. The process for removing oxygen from hydrocarbon-containing gas mixtures as claimed in claim 1, wherein the gas mixture exiting the reactor has a temperature of from ≤350° C. to ≥100° C.

6. The process for removing oxygen from hydrocarbon-containing gas mixtures as claimed in claim 1, wherein the gas mixture exiting the reactor contains ≤1% by volume of oxygen, from 60 to 99.99999% by volume of one or more hydrocarbons and optionally one or more further gases selected from the group consisting of nitrogen, noble gases, hydrogen, carbon dioxide, carbon monoxide and water, where the percents by volume are based on the total volume of the respective gas mixture and add up to a total of 100% by volume.

7. The process for removing oxygen from hydrocarbon-containing gas mixtures as claimed in claim 1, wherein the degree of conversion of oxygen in the reactor is from 50 to 100 mol %.

8. The process for removing oxygen from hydrocarbon-containing gas mixtures as claimed in claim 1, wherein the gas mixture exiting the reactor contains from 85 to 99% by weight of the hydrocarbons which were present in the hydrocarbon-containing gas mixture to be purified which was introduced into the reactor.

9. The process for removing oxygen from hydrocarbon-containing gas mixtures as claimed in claim 1, wherein the gas mixture exiting the reactor is conveyed in its entirety or in part through a countercurrent heat exchanger in which the hydrocarbon-containing gas mixture is heated and which, after leaving the countercurrent heat exchanger, is fed to the reactor.

10. The process for removing oxygen from hydrocarbon-containing gas mixtures as claimed in claim 1, wherein the gas mixture exiting the reactor is partly fed to further purification or utilization and the remaining part is added to one or more starting gas mixtures,
wherein starting gas mixtures contain ≤15% by volume of oxygen, from 40 to 95% by volume of one or more hydrocarbons and optionally one or more further gases selected from the group consisting of nitrogen, noble gases, carbon dioxide, carbon monoxide and water, where the percents by volume are based on the total volume of the respective gas mixture and add up to a total of 100% by volume.

* * * * *